(12) United States Patent
Geerlings

(10) Patent No.: US 7,374,936 B2
(45) Date of Patent: *May 20, 2008

(54) METHOD AND MEANS FOR SITE DIRECTED THERAPY

(75) Inventor: Maurits W Geerlings, Düsseldort (DE)

(73) Assignee: Actinium Pharmaceuticals, Inc., Florham Park, NJ (US)

(*) Notice: Subject to any disclaimer, the term of this patent is extended or adjusted under 35 U.S.C. 154(b) by 398 days.

This patent is subject to a terminal disclaimer.

(21) Appl. No.: 10/022,631

(22) Filed: Dec. 17, 2001

(65) Prior Publication Data

US 2002/0082389 A1 Jun. 27, 2002

Related U.S. Application Data

(60) Division of application No. 09/014,206, filed on Jan. 28, 1998, now Pat. No. 6,403,771, which is a continuation-in-part of application No. 09/002,848, filed on Jan. 5, 1998, now Pat. No. 6,127,527, which is a continuation of application No. 08/440,857, filed on May 15, 1995, now abandoned, which is a division of application No. 08/097,471, filed on Jul. 27, 1993, now abandoned, which is a continuation-in-part of application No. 07/657,580, filed on Feb. 19, 1991, now Pat. No. 5,246,691.

(51) Int. Cl.
*C12N 5/16* (2006.01)

(52) U.S. Cl. .............. 435/344; 435/344.1; 435/7.2; 435/7.23; 435/330; 436/512; 436/541; 436/548; 436/57; 436/64; 530/413; 530/228

(58) Field of Classification Search .......... 435/7.1–7.2, 435/7.23, 330, 344–344.1; 436/512, 541, 436/542, 548, 57, 64; 530/413, 228; 424/138.1, 424/140.1, 155.1, 181.1
See application file for complete search history.

(56) References Cited

U.S. PATENT DOCUMENTS

| | | | |
|---|---|---|---|
| 4,001,387 A | 1/1977 | Barak et al. | |
| 4,296,785 A | 10/1981 | Vitello | |
| 4,305,922 A | 12/1981 | Rhodes | |
| 4,454,106 A | 6/1984 | Gansow et al. | |
| 4,472,509 A | 9/1984 | Gansow et al. | |
| 4,663,129 A | 5/1987 | Atcher | |
| 4,732,864 A | 3/1988 | Tolman et al. | |
| 4,816,397 A | 3/1989 | Boss et al. | |
| 4,828,991 A | 5/1989 | Hanna et al. | |
| 4,833,329 A | 5/1989 | Quint et al. | |
| 4,894,364 A * | 1/1990 | Greer .................. 514/49 | |
| 4,923,985 A | 5/1990 | Gansow et al. | |
| 5,038,046 A | 8/1991 | Norman et al. | |
| 5,246,691 A * | 9/1993 | Geerlings et al. | |
| 5,254,328 A | 10/1993 | Herscheid et al. | |
| 5,292,868 A * | 3/1994 | Subramanian ........ 530/391.5 | |
| 5,296,216 A * | 3/1994 | Turner .................. 424/53 | |
| 5,355,394 A | 10/1994 | Van Greel | |
| 5,428,154 A | 6/1995 | Gansow et al. | |
| 5,443,816 A * | 8/1995 | Zamora et al. ........ 424/1.69 | |
| 5,641,471 A | 6/1997 | Geerlings | |

FOREIGN PATENT DOCUMENTS

EP 0306168 8/1988
WO WO 90/15625 * 12/1990

OTHER PUBLICATIONS

Macklis et al. Radioimmunotherapy with alpha-particle-emitting immunoconjugates. Science (1988), vol. 240, No. 4855, pp. 1024-1026.*
Rotmensch et al. Estimates of dose to intraperitoneal micrometastases from alpha and beta emitters in radioimmunotherapy. Gynecologic Oncology (1990), vol. 38, No. 3, pp. 478-485. .*
D.S. Wilbur, "Potential Use of a α-emitting Radionucleotides in the Treatment of Cancer", *Antibody, Immunoconjugates and Radiopharmaceuticals*, 4(1): 85-97 (1991).
T. Mitsugashira et al., "Preparation of Traces for Actinium, Thorium, Proactinium and Uranium", *SPEY*, Min. Educ. Sci. & Cult., Tokyo, 9: 111-116 (1984).
S. Suzuki, "Solution Chemistry of Light Actinude Elements", Japan—US Seminar on Torium fuel reactors—Proceedings, Nara, Japan, Oct. 18-22, 1982 (Tokyo, 1985), pp. 137-143.
S. Mirzadeh et al., "Radiometal Labeling of Immunoproteins: Covalent Linkage of 2-(-4Isothiocyanatobenzyl)diethylenetriaminepentaacetic Acid Ligends to Immunoglobulin", *Bioconjugate Chem.*, 1: 59-65 (1990).
Zwierzina et al., *Stem Cells*, 11: 144 (1993).
Kozak et al., *Tibtech*, 4(10): 259 (1986).
Goldenberg, *Arch. Pathol. Lab Med.*, 112: 580 (1988).
M. Chatterjee et al., *Cancer Immunol. Immunopathol.*, 38: 75-82 (1994).
Osband, *Immunol. Today.* 11(6): 193-195 (1990).
Curti, *Crit. Rev. Oncol. Hematol.*, 14: 29-39 (1993).
Jain, *Scientific American* 271: (1): 58-65 (1994).
D.R. Fischer, "Alpha-Particle Emitters in Medicine", Proceedings of a symposium held at Loews L'Enfant Plaza Hotel, Washington, DC, Sep. 21 and 22, 1989, pp. 194-214.

(Continued)

Primary Examiner—Bao-Thuy L. Nguyen
(74) Attorney, Agent, or Firm—Wilmer Cutler Pickering Hale and Dorr LLP

(57) ABSTRACT

The present invention relates to the field of site directed therapy. More specifically the invention relates to site directed radio therapy, and provides a method for production of radioconjugates and an apparatus for radioimmunotherapy. The method, conjugates and apparatus can be practicalized without the need for radioactive shielding and/or airtight facilities. Without these restrictions the invention provides a simple and efficient means of therapy at the bed-side of the patient.

9 Claims, 3 Drawing Sheets

OTHER PUBLICATIONS

M.R. McDevitt et al., "Alpha Particle Emitting Bismuth-213 Cyclohexylbenzyl DTPA Constructs of Monoclonal Antibodies for Therapy of Cancer", *Cancer Res.*, 1998.

M. Brechbiel and O.A. Gansow, Synthesis of C-Functionalized *trans*-Cyclohexyldiethylenetriaminepenta-acetic Acids for Labelling of Monoclonal Antibodies with the Bismuth-212 α-Particle Emitter, *J. Chem. Soc. Perkin Trans.*, pp. 1173-1178 (1992).

Scheinberg et al., "Targeting in Erythroleukemic Mice . . . ", Monoclonal Antibodies Drug. Dev., Process Jacob Abel Symp. for Drug Dev., pp. 159-171 (1982).

"Astatine-211: It's Possible Applications in Cancer Therapy", Brown, *International Journal of Radiation Applications and Instrumentation*, Part A, vol. 37, No. 8, pp. 789-798 (1986).

"Preparation of $^{224}$RA for Therapy of Ankylosing Spondylitis", Delikan Health, Physics, vol. 35, No. 1, pp. 21-24 (1978).

Lambrecht, "Radionuclide Generators", Radiochimica Acts 34, 9-24 (1983), R. Oldenbourg Verlag, Munich, p. 19.

Spitsyn & Mikheev, "Generators for the Production of Short-Lived Radioisotopes, " Atomic Energy Review, 9(4): 787 et seq. (1971), International Atomic Energy Commission, Vienna, pp. 820-823.

Riechmann et al., "Reshaping human antibodies for therapy", Nature, 332:323-327 (1988), Macmillan Magazines, London.

DeNardo et al., "Fractionated Radioimmunotherapy of 8-Cell Malignancies with $^{131}$I-Lym-1", Cancer Res. (Suppl), 50: 1014s-1016s (1990).

\* cited by examiner

METHOD AND MEANS FOR SITE DIRECTED THERAPY

The present application is a division of allowed U.S. patent application Ser. No. 09/014,206, filed Jan. 28, 1998, which is a continuation-in-part of application Ser. No. 09/002,848, filed on Jan. 5, 1998, and now U.S. Pat. No. 6,127,527 issued on Oct. 3, 2000, which is a continuation of U.S. patent application Ser. No. 08/440,857, filed May 15, 1995, now abandoned, which is a division of U.S. patent application Ser. No. 08/097,471, filed Jul. 27, 1993, and now abandoned, which is a continuation-in-part of U.S. patent application Ser. No. 07/657,580, filed Feb. 19, 1991 and now U.S. Pat. No. 5,246,691. The entire disclosures of all of the above-mentioned patent applications are incorporated by reference in the present specification as though set forth herein in full.

The present invention relates to the field of site directed therapy. Nowadays there are a number of methods of site directed therapy which have been suggested to eliminate unwanted cells or other biological matter, e.g., vascular occlusions, or infectious organisms from the body of a mammalian subject.

There are many fields of therapy in which such methods may be applied. The most important ones include, without limitation, immune diseases (either auto immune diseases or acquired immune diseases), cancer and viral or microbial infections.

Site directed therapy is a method whereby a cytotoxic compound is delivered to the immediate vicinity of the target cell or infectious organism. This is usually done by coupling a targeting moiety to the cytotoxic compound.

This targeting moiety recognizes a structure in, on, or near the target. Known targeting moieties include, but are not limited to, antibodies, more specifically monoclonal antibodies and more preferably human monoclonal antibodies, nucleic acids, receptor directed ligands and the like.

Cytotoxic compounds can be for instance drugs, such as adriamycin, toxins such as ricin A and radioisotopes.

Radioisotopes can be used not only for therapy, but also to identify the site-or sites of the target (imaging). This invention provides methods of therapy and imaging using a conjugate of a targeting moiety and at least one radioisotope.

Therapy with targeting moieties is widely known. Targeting can be accomplished by aiming the targeting moiety directly to the wanted site, but it may also be directed to another targeting moiety which is directed to the wanted site (so called pretargeting). Pretargeting offers an advantage over direct targeting when the specificity of the targeting moieties is not sufficient. By using a first localizing moiety followed by a second one coupled to a cytotoxic compound, the amount of cytotoxic compound delivered to non-target sites can be lowered significantly.

Known targeting moieties, such as antibodies, often cannot be provided with a large amount of cytotoxic compounds without hampering their targeting specificity.

Therefore it has often been suggested to use a carrier molecule, such as HSA or a nucleic acid, or a polymer, which can be loaded with a high number of cytotoxic compounds and coupled to a targeting moiety.

All of the above-mentioned variations on the theme of site directed therapy and/or imaging can be used more advantageously with the present invention.

A well established problem in the field of imaging and site directed radiotherapy is to find a suitable radioisotope. Apart from the amount of energy that is released upon their decay, which should be sufficient to be measurable outside the subject in the case of imaging and sufficiently lethal to the target in the case of therapy, there is also a problem in finding an isotope with a suitable half-life.

An isotope with a long half life cannot be chosen because of the biological half life of the targeting moiety, which means that most of the isotopes will decay after disintegration of the conjugate. This decay after the disintegration of the conjugate will lead to cytotoxicity to other cells or tissues than the target.

Furthermore, all conjugates which do not localize will be secreted from the body and present a radio active waste problem.

It is also not practical to choose a radioisotope with too short a half life, because of packing and shipping delays and because the institution carrying out the therapy must be equipped to make the conjugate, transport it to the patient and administer it in a very short interval of time, otherwise most of the radioisotope will have decayed before entering the body, let alone localization at the target site.

The isotopes used for imaging usually are gamma emitting isotopes, for therapy auger electron emitting $\alpha$-$\beta$-emitting, or $\alpha$-emitting isotopes may be used.

Most preferred for the present invention are $\alpha$-emitting isotopes.

The short-range cell-killing effect of $\alpha$-particles is enormous: a 1 mm diameter tumor, comprising maybe 600,000 cancer cells needs about 6 $\alpha$-particles of 6 MeV per cell to deliver a dose of 600 red, causing a 99.9% cell-kill ratio, and that specifically because of the stochastic nature of the hit-and kill-mechanism.

However, due to the same stochastic nature, a 10 times lower a-radiator dose will enhance the cell survival ratio with a factor 500: more than 50% of the cells (or non-tumor cells in similar morphology for that matter) would survive a 60 red $\alpha$-radiation dose, equivalent to 0.6 $\alpha$-particles per cell.

This characteristic would make an effective $\alpha$-radioimmunotherapy within reach, provided that a "quality factor" for the isotope-antibody conjugate of 10 or better can be obtained. It is the purpose of the present invention to contribute towards this goal in a most essential manner.

The quality factor is a ratio between localized antibody at the target site, divided by the antibody "sticking" to other tissue.

The notion of using $\alpha$-particle emitting radioisotopes as agents for the killing of tumor cells was already mentioned in the literature during the mid-fifties. Since then other potential candidate isotopes were and are being proposed, of which a good summary is given by Fisher (1) and by Wilbur (2) which brings the list to (with their half-lives between parentheses): $^{223}$Ra (11.4 d), $^{225}$Ac (10 d), $^{224}$Ra (3.6 d), $^{225}$Fm (20 h), $^{211}$At (7,2 h), $^{212}$Bi (60 m), and $^{213}$Bi (47 m)

Although important publications appear regularly in the literature regarding microdosimetry, antibody isotope coupling techniques, pre-clinical in vitro and in vivo experiments, no clearly defined, larger scale clinical experiments are being done until now, for a variety of reasons:

a. very few human monoclonal antibodies with proven sufficient quality are available yet, b. very limited biological safety data are available for antibody coupling agent (the latter for the binding of the radioisotope) combinations, c. some isotopes may not become available for large scale application at acceptable cost prices ($^{225}$Fm), d. isotopes may be too difficult and therefore too expensive to obtain because of the necessary procurement process ($^{211}$At from $^{209}$Bi by a ($\alpha$, 2n) reaction in a cyclotron and subsequent isolation plus purification), e. other isotopes do have a Rn-isotope as first daughter in their decay sequence, allowing redistribution of daughter nuclei before decay ($^{224}$Ra, $^{223}$Ra), and also necessitating gas-tight reaction conditions, f. some isotopes may have a relatively long living daughter isotope somewhere in their decay sequence ($^{224}$Ra, $^{223}$Ra, $^{225}$AC) also with the chance that daughters thereof may redistribute before decay, g. the radioactive halflife of some isotopes is so long that most of the activity leaves the patient undecayed, resulting in a waste problem ($^{223}$Ra, $^{224}$Ra $^{225}$AC) or h. the halflife of the isotope is so short that most of the isotope decays before reaching its ultimate target ($^{212}$Bi, $^{213}$Bi), i. sufficient precursor material may not be available to extract at one time the necessary amount of isotope for a single patient treatment ($^{212}$Bi, $^{213}$Bi), and, j. isotopes producing hard gamma rays in their isotope decay need shielding facilities to prevent radiation hazards to technicians and nursing personnel.

One or more of the arguments listed above will make it very difficult, if not impossible for some of the isotopes to ever be used on a large scale for $\alpha$-radio-immunotherapy, and that in particular if one or more of the others can be used on acceptable technical, logistical and financial conditions.

The closest prior art to the present invention (the French patent application FR-A-2 527 928) discloses a method to produce conjugates of an antibody and $^{212}$Bi. However, these conjugates still suffer from the drawbacks mentioned above under e, h, i and j.

SUMMARY OF THE INVENTION

The present invention provides a therapeutic radioconjugate of a targeting moiety bound, directly or indirectly, to at least one relatively short lived $\alpha$-particle emitting radioisotope, the targeting moiety being effective to deliver the conjugate to a pre-determined pathological-site in a mammal. The pathological site comprises a target moiety, which together with the targeting moiety, constitutes a specific binding pair.

The targeting moiety is preferably selected from the group consisting of an antibody, or antibody fragment which bind specifically to a cell-surface antigen; or a ligand or ligand fragment which bind specifically to a cell surface receptor.

The pathological site may comprise diseased cells, e.g., tumor cells, cells at an inappropriate site, e.g., neutrophils at site of inflammation, platelets at sites of injury, or it may be an extracellular structure, such as fibrin or thrombin within a coronary vessel at a site of infarct, cholesterol at a site of atherosclerotic placque, calcification in diseased vessels, amyloid plaque at disease sites in the brain, or the like.

Also according to this invention, a method is provided for preparing the above-identified therapeutic radioconjugate. The method involves loading onto a binding medium a relatively long lived radioisotope, the decay sequence of said relatively long lived radioisotope yielding daughter isotopes that emit predominantly $\alpha$-and/or $\beta$-particles without harmful gamma radiation, eluting said $\alpha$-particle emitting radioisotope from said binding medium and coupling said $\alpha$-particle emitting radioisotope, substantially free of said relatively long lived radioisotope, to said targeting moiety.

Relatively long lived means that the radioisotopes have a decay time in the order of several days, which enables sufficient time for packing and shipping. Relatively short lived in this context means that the radioisotopes have a decay time in the order of minutes or hours.

The reference to a decay sequence in which predominantly $\alpha$ and/or $\beta$-rays are emitted is meant to signify a decay sequence which does not cause danger for radiation hazards caused by gamma rays to people working with the compounds without the burden of applying protective shielding.

Preferably, the relatively long lived isotope is $^{225}$Ac and the relatively short lived $\alpha$-particle emitting radioisotope is $^{213}$Bi.

An eluent containing a targeting moiety passes from a vessel (1) through an ion exchange column (3), containing a bound parent radiometal, wherein a daughter radioisotope binds to the targeting moiety. The eluent containing the conjugate is mixed with infusion liquid from vessel (2) at junction (6) and administrated to the patient (4). Optionally, there is additional length of tubing between column (3) and junction (6) to correct for the half lives of intermediate daughter isotopes.

Figure 2:
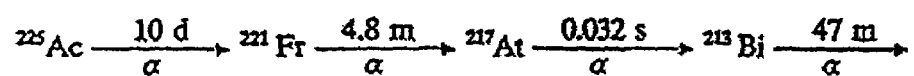

FIG. 2 depicts the decay chain of $^{225}$Ac.

Figure 3:
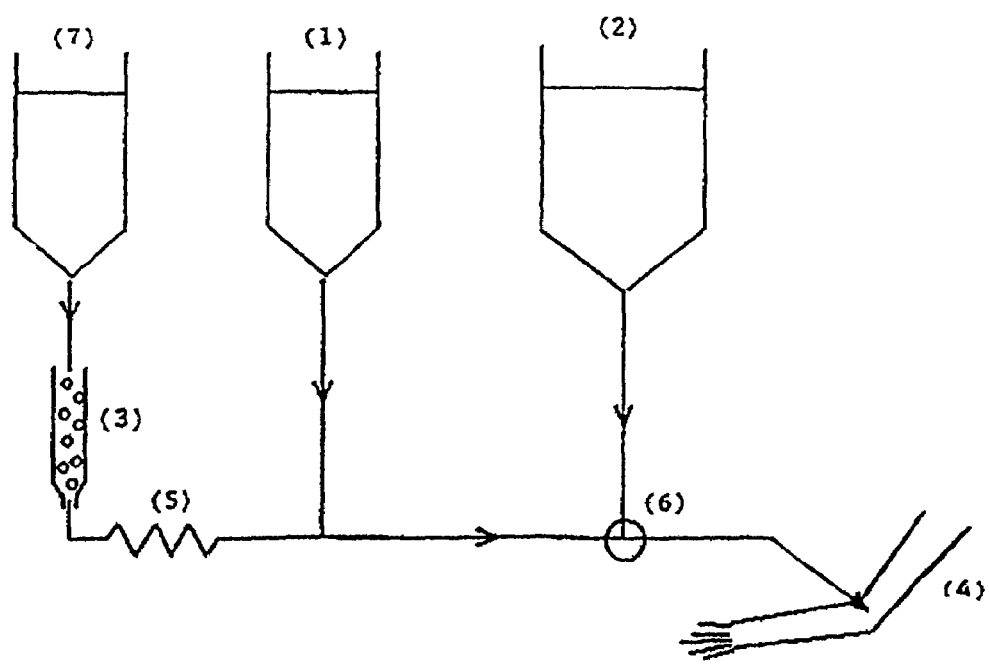

FIG. 3 depicts another apparatus which may be used in practicing this invention.

An eluent passes from a vessel (7) through an ion exchange column (3) where a daughter radioisotope is stripped from that column.

The eluent containing the isotope is mixed with a liquid from a vessel (1) containing a targeting moiety, so that the isotope becomes bound to the targeting moiety. The resulting fluid is mixed with infusion liquid from vessel (2) at junction (6) and administered to the patient (4). Optionally the eluent containing the isotope may be lead through an additional length of tubing (5) to correct for the half-life of intermediate daughter isotopes.

Figure 4:
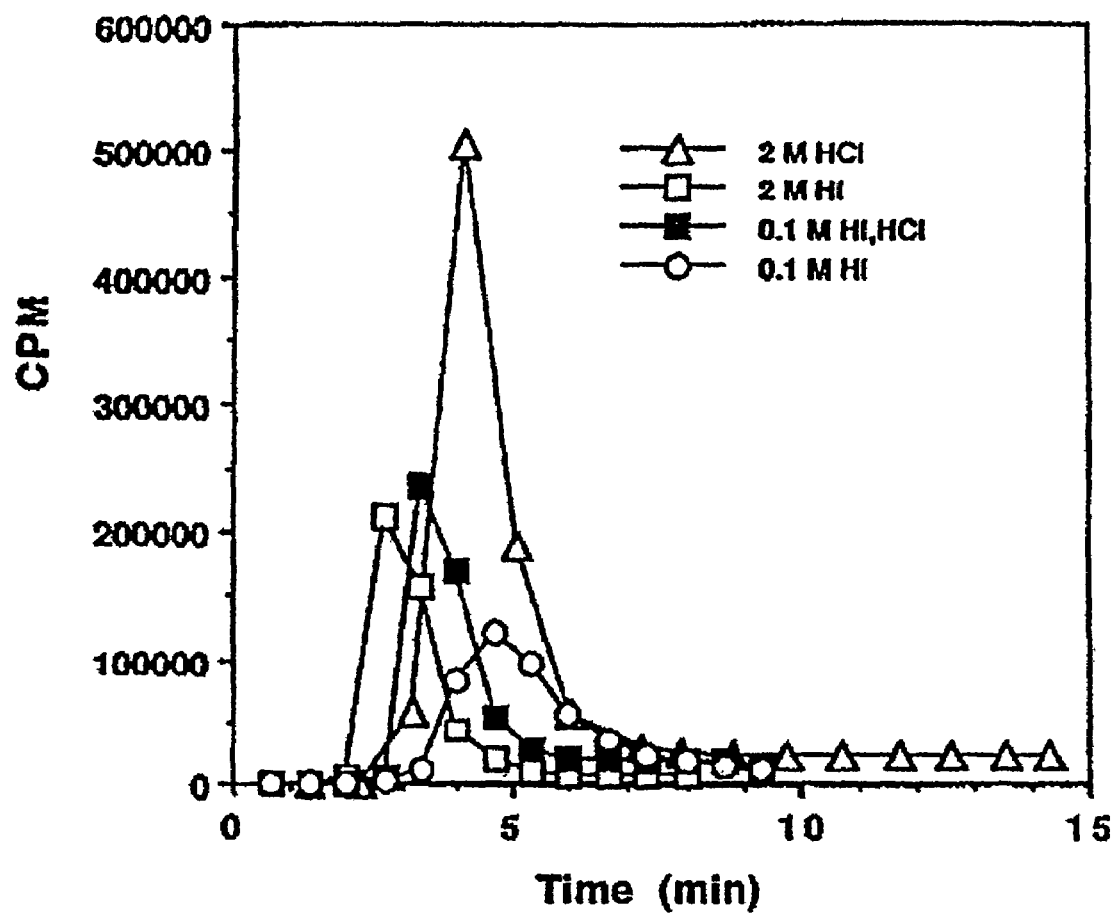

FIG. 4 shows the elution behavior of $^{213}$Bi at several HCl and HI concentrations.

DETAILED DESCRIPTION OF THE INVENTION

An important aspect of the present invention is that the radioconjugate can be made or quasi be made at the site of therapy. Due to the decay sequence which results mainly in $\alpha$- and/or $\beta$-radiation it has become possible that no protection against radiation is necessary. This is extremely useful, because due to the absence of gamma radiation it has become possible that the conjugation can be done at the bed side or in a nearby nuclear medicine lab without the necessity to apply radiation shielding or isolation of the patient or the equipment. This is not only preferable from the point of radiation danger but is also gives advantages for the availability of the short-living isotope. This isotope can be prepared in the neighborhood of the patient allowing for a rapid administration and prevention of loss of therapeutic action caused by the rapid decay of the isotope. In this way it has become possible to use short lived radioisotopes for therapy.

Figure 1:
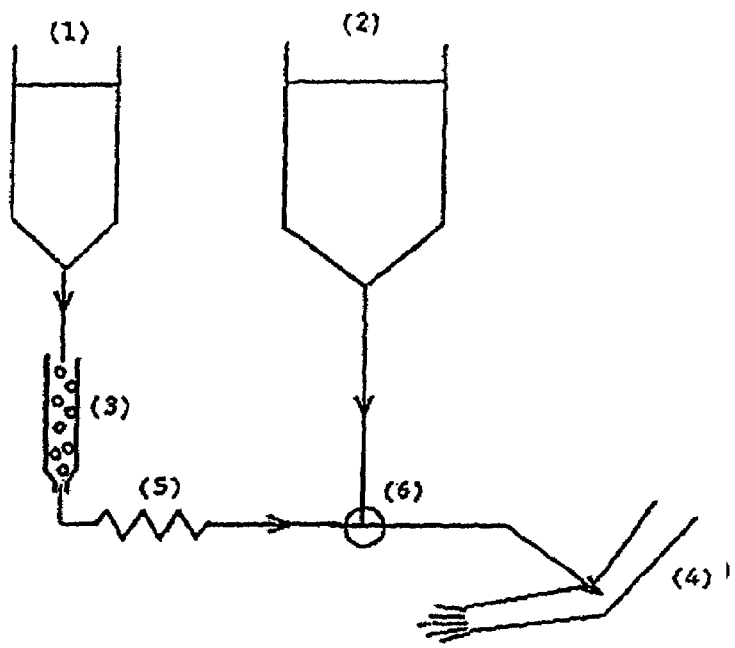
FIG. 1 depicts an apparatus which may be used in practicing this invention.

An ion exchange column or another appropriate substrate filled with the long lived isotope can be placed at or near the bedside, for instance, where the short-lived isotope can be eluted by washing the substrate with a suitable solution. After elution the short lived isotope is coupled to the targeting moiety and (optionally together with an infusion solution) the conjugate can be administered. This can all be done in a continuous mode with an apparatus according to the invention as shown in FIG. 1 or FIG. 3, or in an intermittent mode by using ordinary laboratory glassware.

Of course it may also be made possible to add the targeting moiety to the eluting solution so that the coupling takes place in the column.

As noted above, the targeting moiety of the radioconjugate and the target moiety of the pathological site constitute a specific binding pair. The expression "specific binding pair", as used herein refers to complementary substances that selectively recognize and interact with one another, to the substantial exclusion of other substances. Representative examples of specific binding pairs include, without limitation, antibodies (which may be monoclonal or polyclonal immunoglobulins or immunoreactive fragments thereof) and cell-associated targets, such as membrane-bound proteins or glycoprotein, including cell surface antigens of either host cell or viral original or histocompatibility antigens; ligand or ligand fragment and receptor; hormone-receptors and lectin-receptors.

The invention is described hereinbelow with particular emphasis on the use of antibodies as the targeting moiety of the radioimmunoconjugate of the invention. It should be understood, however, that any of the other targeting moieties described above may also be used to effect site directed delivery of the radioconjugate.

This invention primarily addresses the use of the shortest-lived isotope from the list mentioned above, $^{213}$Bi. The invention enables the person skilled in the art to milk this isotope by a continuous or an intermittent extraction-method from one of its precursors, $^{225}$Ac, at the bed-side of the patient, or in the nearestby hospital laboratory facility, to link the $^{213}$Bi in a continuous or an intermittent manner onto the targeting moiety, to either or not mix the conjugate solution with an infusion liquid and to administer this mixture intravenously to the patient for example as is schematically pictured in FIG. 1.

At first sight this procedure might seem extremely wasteful, because $^{225}$Ac, itself being an α-emitting isotope, produces three potentially therapeutically useful α-particles before yielding the $^{213}$Bi-isotope, as is shown in FIG. 2. However, the source material for $^{225}$Ac, $^{229}$Th, and thereby also the $^{225}$Ac itself, can be made available at sufficiently low cost to allow it to be used in the proposed manner on economically justifiable terms.

The use of $^{213}$Bi is not only preferable from a viewpoint of radiation hazards. It is also preferable because no gaseous isotopes occur in the decay sequence of its precursors. This is advantageous over the use of other isotopes which have a decay with a gaseous isotope which necessitates the handling and reaction environment to be air-tight. Milking, conjugation and administration of $^{213}$Bi are not hampered by the necessity for having air-tight conditions and the reactions can be done under normal conditions.

The targeting moiety may preferably be a monoclonal antibody, or a fragment or a derivative thereof. Preferably such an antibody is a human or a humanized antibody to prevent immunologic reactions to the antibody. Non-human antibodies are mostly of murine origin. These, like all other foreign proteins, are highly immunogenic in man. The phenomenon of HAMA and of HAHA, is well known in the field and severely limits the use of mouse derived antibodies in diagnostic and especially in therapeutic applications in human beings. A single application of a murine antibody is usually sufficient to mount an immune response that will prevent subsequent applications to be effective.

Of course fragments and/or derivatives of the targeting moieties can also be used, as long as they retain a substantial amount of target specificity. Thus, for this invention it should be understood that where a targeting moiety is mentioned one should also consider a fragment or a derivative thereof, as well as any other appropriate site-selective moiety, as part of the invention.

Preferably antibodies are directed against tumor associated antigens, such as CEA (Carcino-embryonic antigen), AFP (alpha-foetoprotein), PHAP (fast homoarginine-sensitive alkaline phosphatase), p97 (melanome specific), and EL-1 (elongation factor 1).

Another preferable targeting moiety is formed by a ligand for a cell surface receptor or a fragment or derivative of such a ligand. Examples of such ligands are agonists and/or antagonists of pharmacologically active receptors, but also T cell epitopes which can bind to the T cell receptor are preferred.

Another aspect of the invention provides a method for treating numerous patients with one ion exchange column loaded with isotope. The amount of isotope loaded depends on the number of patients to be treated. The wanted isotope can be eluted from the column intermittently, with suitable intervals depending on the half-lives in the decay chain.

With related tumours or infectious organisms the same targeting moiety (or mix of targeting moieties) may be used for various patients. For unrelated diseases there must be a means for changing the targeting moiety preparation.

The coupling of the isotope to the targeting moiety can be done in any suitable way, as long as the targeting specificity of the targeting moiety is not hampered to a substantial amount.

Preferably the coupling will be done through one of the now many known chelating agents. As already disclosed, it may be advantageous to couple the isotopes to a carrier, such as HSA, which of course can also be done through chelating agents. The advantage of a carrier is that a large number of radioisotopes can be brought to the target cell. Since it is assumed that several α-particles are necessary for the destruction of one target cell an increase in the number of isotopes in the direct neighborhood of the target cell is preferable.

The invention also provides a conjugate as produced by the method of the invention, as well as a pharmaceutical formulation comprising such a conjugate.

A method is provided for producing the conjugate of a targeting moiety and a radioisotope and administering it to the patient without delay or any necessary actions of the therapist.

Another aspect of the invention provides an apparatus for carrying out site directed therapy or imaging.

The simplest way to describe the method and apparatus, subject of this invention, with reference to FIG. 1, is as follows:

A capillary column contains, by means of example, twice the amount of precursor-$^{225}$Ac needed for a single patient dose of $^{213}$Bi. Example: in a case the patient dose corresponds with 30 mCi (equals $2.10^{-9}$ g) of $^{213}$Bi over a 10 day period, the capillary column (3) will contain 200 µCi of $^{225}$Ac (equals $4.10^{-9}$ g).

The $^{225}$Ac is present in a 3+ form on a suitable ion exchange substrate. Upon its (continuously occurring) decay it is stripped from the column by a certain overdose of the eluent in flask (1) containing the appropriate targeting moiety capable of binding the isotope. The binding part of the targeting moiety and other chemical equilibrium conditions of the eluent-ionexchange system are chosen such that the $^{213}$Bi, for all practical purposes, quantitatively binds to the targeting moiety. The immediate daughter of $^{225}$Ac, $^{221}$Fr has a radioactive decay halflife of 4.8 minutes. It is this isotope which acts via the very short-lived $^{217}$At as the direct precursor of $^{113}$Bi. In case the $^{221}$Fr is not retained by itself or in the ion exchange substrate, the delaying effect of the $^{221}$Fr-halflife causes the need of a certain period of time between the decay of $^{225}$Ac at and its stripping from the capillary column and the binding of the 213Bi onto the targeting moieties. The optimum value for such a delay is somewhere between the halflife of the $^{221}$Fr and the halflife of the $^{213}$Bi isotopes.

This delay can be effected by the length of tubing between the capillary (3) and the patient (4), if necessary enhanced by an extra length of intermediate tubing, as indicated in FIG. 1 as (5). The infusion liquid from flask (2) enters the patient, it is mixed with the isotope-containing eluate from column (3), as indicated as junction (6) in FIG. 1.

In order to obtain optimal stripping and conjugation conditions in the capillary column (3), it may be that the composition of the eluent in flask (1) is not optimal (for example its pH-value) for administration to the patient. Presuming that the volume rate of infusion liquid is an order of magnitude higher than of the eluate liquid, this can easily be countered for by a compensating off-balance (buffered) pH-value of the infusion liquid.

It is also possible that the binding of the targeting moiety is hampered by the physico-chemical properties of the eluent. Therefore, an other embodiment of the invention is represented in FIG. 3 where an eluens is lead from a vessel (7) through an ion exchange column (3) so that a radioisotope is stripped from that column. The eluens containing the isotope is mixed with a liquid from a vessel (1) containing a targeting moiety, so that the isotope is bound to the targeting moiety. The resulting fluid is mixed with infusion liquid from vessel (2) at junction (6) and administered to the patient (4). Optionally the eluens containing the isotope may be lead through an additional length of tubing (5) to correct for the half-life of intermediate daughter isotopes.

What the invention enables in terms of the development and the clinical use of α-radioimmuno therapy, in this case using $^{213}$Bi as the active cell killing agent is:

"single patient kits" in the form of precursor with a halflife that is logistically manageable regarding:
minimization of active material loss by radio active decay during operations like packaging, transport, etc.,
safety in transportation over long distances and in handling in hospitals,
applicability in practice on a large scale in many hospitals without need for special precautions, regarding:
the handling of the material and the application procedures regarding the treatment of patients, all without complicated monitoring equipment,
collection and handling facilities for (urinous) waste,
maximal (and in case of continuous extraction, almost total) use of the $^{213}$Bi after it is generated from the precursor isotope,
maximum flexibility in dose administration by the possibility of changing treatment time, allowing for a minimum range of single patient kit precursor concentration standards.

All these aspects then pertain precisely to fields where the short-range α-particles are most suited for their potential therapeutic uses like:

micrometastases (of less than 1 mm diameter) of various cancers,
cellular cancers like leukemias and
also, certain kinds of very localized autoimmune diseases, all of which can essentially be directly addressed either by the blood circulation system or locally without the need for slow diffusion processes of the antibody ligand-isotope complexes through intercellular space in order to find their ultimate destination.

The radioconjugate of the invention may be used not only for treating cancer, immune or infectious diseases, but also for the treatment of inflammatory conditions, such as rheumatoid arthritis, arteritis, endometritis or the like, as well as for the removal of new growths or other abnormal tissue. These radioconjugates are also useful for the detection of pathological, extra-cellular structures, including, without limitation, fibrin or thrombin within a coronary vessel at a site of infarct, cholesterol at a site of atherosclerotic placque, calcification in diseased vessels, amyloid plaque at disease sites in the brain, or the like.

A special advantage of intermittent administration of the therapeutic radioconjugates is the advantage which occurs by dose fractionation. Statistically it is possible to calculate the dose needed to kill 99.9% of the tumor cells with a dose of radioconjugate: assuming that a leukemic (monocellular, blood and bone marrow) tumor load of 1 kg exists, which is roughly equal to $10^{12}$ cells, and that 10 α-particles are needed to kill a cell (6 MeV), then $10^{13}$ α-particles would be needed, which corresponds with 50 mCi $^{213}$Bi. Thus for a single dose, which would kill 99.9% of the tumor cells 50 mCi $^{213}$Bi would be needed.

The "dose versus survival" relation for this cell morphology with 6 MeV a-particles can be derived from the formula D/Do=−1n S, in which S=survival fraction, D=dose administered and $D_o$=reference dose for 37% survival. From this formula the following Table of values can be calculated:

TABLE 1

Dose versus kill ratio for tumor cells. The numbers are the number of α-particles necessary to kill the given % of tumor cells. In case A 600 rad are necessary to obtain a 99% kill ratio. In case B 2000 rad is assumed necessary for the same effect.

| Cell kill in % | Case A | Case B |
|---|---|---|
| 0 | 0 | 0 |
| 1 | 0.015 | 0.05 |
| 10 | 0.15 | 0.5 |
| 40 | 0.7 | 2 |
| 50 | 1 | 3 |
| 60 | 1.3 | 4 |
| 70 | 1.5 | 5 |
| 90 | 3 | 10 |
| 99 | 6 | 20 |
| 99.9 | 9 | 30 |
| 99.99 | 12 | 40 |
| 99.999 | 15 | 50 |

From this Table the effects of an intermittent, dose fractioned, administration can be read:

The effect of cell survival of successive doses of 5 mCi $^{213}$Bi in case A is as follows:
the first dose of 5 mCi equals 1 α-particle per cell, which gives 50% survival, which means that $0.5 \cdot 10^{12}$ cells remain;
the second dose of 5 mCi equals 2 α-particles per cell, which gives 20% survival, which means that $0.1 \cdot 10^{12}$ cells remain;

the third dose of 5 mCi equals 10 α-particles per cell, which gives 0.1% survival, which means that $0.1 \cdot 10^9$ cells remain;

the fourth dose of 5 mCi equals 10,000 α-particles per cell, which means a total kill.

Thus it can be shown that by intermittent dosing a total dose of 4 times 5=20 mCi $^{213}$Bi is sufficient to give a total kill of the tumor cells. For clarity the effects of intermediate tumor growth and maximization of the number of targeting moieties on the tumor cells have been omitted. Nevertheless, it is clear that by intermittent administration the total load of radioactive material can be kept smaller.

Even in case B, which has a more unfavourable dose versus survival rate, and advantageous effect is realized:

1st dose→1α/cell→75% survival→$0.75 \cdot 10^{12}$ cells
2nd dose→1.3α/cell→70% survival→$0.50 \cdot 10^{12}$ cells
3rd dose→2α/cell→60% survival→$0.30 \cdot 10^{12}$ cells
4th dose→3α/cell→50% survival→$0.15 \cdot 10^{12}$ cells
5th dose→6α/cell→25% survival→$0.04 \cdot 10^{12}$ cells
6th dose→25α/cell→0.3% survival→$0.1 \cdot 10^9$ cells
7th dose→10,000α/cell-total kill after 35 mCi.

There are two ways presently known to obtain $^{229}$Th as a precursor for the $^{225}$Ac-source-isotope:

from stockpiled 233U, by its natural a-decay. Batches of $^{233}$U were made in nuclear breeder reactors about 30 years ago, but never used as nuclear fuel.

Some of the $^{233}$U was separated from the bulk 233Th, from which it was made, so that the now available $^{229}$Th can be obtained in highly pure form.

by high neutron flux irradiation from natural $^{226}$Ra, with $^{227}$Ac as an intermediate product. Further irradiation of this $^{227}$Ac yields roughly equal amounts of $^{229}$Th and $^{228}$Th, the latter with much shorter halflife (2 years) than the $^{229}$Th. On the one hand this complicates the extraction of $^{225}$Ac considerably, but in properly equipped installations it may on the other hand yield $^{224}$Ra, an α-emitter with a 3.7 day halflife. When the Ra is properly isolated, it may be used as a source for 212Pb.

The 10.5 hour halflife of $^{212}$Pb will cause considerable complications in handling. However, when these are properly taken care of, one may envisage to use the $^{212}$Pb-isotope in the same manner as the $^{225}$Ac in this invention as a bed-side source of $^{212}$Bi, which for all practical purposes acts as an α-emitter with a halflife of 1.0 hour.

EXAMPLES

Example 1

The separation chemistry of the various radioactive elements mentioned in the text before has been sorted out decades ago and is well-documented in the public literature. Examples are references (3) and (4). $^{225}$Ac can be separated from $^{229}$Th on a Dowex 50 ionexchanger by stripping with 4N HNO$_3$. After evaporation of the acid, the $^{225}$Ac can be dissolved again in 0.5N HNO$_3$ in a fixed concentration and absorbed in the appropriate amount on Dowex 50, which then becomes the material in the mini-column (3) of FIG. 3.

Example 2

0.68±0.07 mCi of $^{225}$sAc was obtained from the European Joint Research Centre. This was loaded on a MP-50 cation exchange resin (Bio-Rad). The formed $^{213}$Bi was eluted with a mixture of 50:50 10% NH$_4$Ac:MeOH with a pH of 6.75.

An autoburet was used to deliver 35 µl of eluant per minute; alternatively, manual elution was done at 50 µl amounts of eluant per minute.

In a few experiments, it was necessary to purify the $^{213}$Bi. This was accomplished by heating the eluant to dryness in a 10 ml beaker containing 0.5 ml of conc. HNO$_3$. After evaporation under an IR lamp, the bismuth activity was transferred to a column of MP-50 resin (2×30 cm, pre-equilbrated with 0.1M HNO$_3$). The resin was washed with 0.2 ml H$_2$O. Then the $^{213}$Bi was eluted with 0.5 ml of Hcl and HI. Various concentrations of Hcl and HI have been tried. FIG. 4 shows the elution patterns for $^{213}$Bi. In all cases, the elution is rapid and quantitative. All of the isotope can be obtained within 5 to 10 minutes after the start of the elution.

Elution of $^{213}$Bi from 225Ac can also be done with generators containing 25 mCi of $^{225}$Ac, as is now the routine practice at Sloan-Kettering in New York City for the ongoing clinical phase-1 trial (the first one ever with systemically administered α-emitting isotope, $^{213}$Bi) against acute myelogenous leukemia. The procedure used is simple: Elution with 0.1 Mol HCl/HI suffices to quantitatively yield larger than 15 mCi samples of $^{213}$Bi free of $^{225}$Ac and of $^{221}$Fr.

Example 3

Radiolabeling was done by adding enough 3M NH$_4$Ac to the $^{213}$Bi stock to achieve pH 4.0-5.0. Then 53 µl or 106 µl of a 4.7 mg/ml solution of monoclonal antibody B3 coupled with the chelator CHX-DTPA (cyclohexyldiethylenetri-aminepenta acetic acid) according to the method described in (5) were gently mixed into the solution. After a fifteen minute reaction time, 1.5 µl of 0.1M EDTA were added. The solution was transferred to a 1 ml syringe with 0.2 ml wash. The solution was then injected into the HPLC (high pressure liquid chromatography) having a TSK 3000 column. The buffer was 0.02 M MES/Cl-(MES=morpholino ethane sulfonic acid), 0.15 M NaCl, pH 6.5. Elution of the B3 antibody occurred at 7.5 minutes. The amount of $^{213}$Bi incorporated into the antibody was monitored with an in-line radiochemical detector (Beckman). All activity measurements of $^{213}$Bi were corrected for decay (t$_½$=45.6 min). Results are depicted in Table 2. Activities of $^{225}$Ac, $^{221}$Fr or $^{217}$At were not detectable in any of the $^{213}$Bi elution products.

Radiolabeling can also be carried out using 15 mCi samples of $^{213}$Bi with a 1000-fold overdose of HuM195 monoclonal antibody, coupled with a further overdose of chelator CHX.A.DTPA, basically according to the method described in (5) and (6). This is the procedure now employed at Sloan-Kettering in New York City. After 10 minutes reaction time, the product is separated from remaining free $^{213}$Bi using HPLC with a TSK 3000 column. Less than 5% of the $^{213}$Bi is lost in remaining free isotope. Due, to decay during the delay caused by these procedures, about 10 mCi of antibody-bound $^{213}$Bi is available for therapy.

TABLE 2

Results of radiolabeling experiments incorporating 213Bi into mAb B3-CHX-DTPA

| Acid | Vol. acid µl | µg mAb | $^{213}$Bi recovered in mAb (%) |
|---|---|---|---|
| 2 M HCl | 210 | 250 | 43.4 (37%) |
| 2 M HCl | 210 | 500 | 45.0 (25%) |
| 0.1 M HCl 0.1 M HI | 500 | 500 | 3.4 (7%) |

Although targeting via coupling of radioisotope to a monoclonal antibody is exemplified in Example 3, the invention is not limited to targeting in this way. Various peptides are known to bind their cognate receptors with high affinity and thus would be suitable ligands for conjugation to the radioisotopes of the invention. Receptors are plasma membrane proteins which bind molecules, such as growth factors, hormones, and neurotransmitters. Tumors develop from particular cell types which express certain subsets of these receptors. Taking advantage of this binding affinity between receptor and ligand enables target-specific delivery of the radionucleotide. Representative examples of receptor-ligand pairs are set forth below:

| RECEPTOR | LIGAND |
| --- | --- |
| epidermal growth factor receptor | epidermal growth factor (53 amino acids) |
| platelet derived growth factor receptor | platelet derived growth factor |
| insulin like growth factor receptor | insulin-like growth factor |
| glucagon receptor | glucagon (29 amino acids) |
| vasopressin receptor | vasopressin (9 amino acids) |
| thyroid stimulating hormone receptor | thyroid stimulating hormone |
| insulin receptor | insulin |

As all of the above-listed ligands are protein molecules, the coupling chemistry set forth in Example 3 is readily adaptable for forming radioimmunoconjugates using these ligands.

REFERENCES (1) D. R. Fisher: "α-particle emmitters in medicine", proceedings of a symposium held at Loews L'Enfant Plaze Hotel, Washington, D.C., Sep. 21 and 22, 1989, pages 194-214, published by the American College of Nuclear Physicians.

(2) D. S. Wilbur: "Potential use of α-emitting radionuclides in the treatment of cancer", Antibody, Immunoconjugates, and Radiopharmaceuticals, Volume 4, No. 1, 1991, pages 85-97, published by Mary Ann Liebert, Inc.

(3) T. Mitsugashira: "Preparation of traces for actinium, thorium, protactinium and uranium", SPEY, Min. Educ. Sci. & Cult., Tokyo, 9, 1984, pages 111-116.

(4) S. Suzuki: "Solution chemistry of light actinide elements", Japan-US seminar on Thorium fuel reactors—proceedings, Nara, Japan, 18-22, October, 1982 (Tokyo, 1985) pages 137-143.

(5) Mirzadeh, S., Brechbiel, M. W., Atcher, R. W., Gansow, O. A. , Bioconjugate Chem., Volum 1, 1990, 59-65.

(6) McDevitt, M. R., Scheinberg, D. A., Brechbiel, M. W. et al., "Alpha Particle Emitting Bismuth-213 Cyclohexylbenzyl DTPA Constructs of Monoclonal Antibodies for Therapy of Cancer", Cancer Res., 1998 (in press)

What is claimed is:

1. A method for killing target cells in a mammal by α-particle radiotherapy, wherein said target cells are in micrometastases having a diameter of about 1 mm or less, said method comprising providing a sufficient quantity of $^{225}$Ac to produce a therapeutically effective amount of $^{213}$Bi through radioactive decay, binding the $^{225}$Ac onto a substrate for immobilizing $^{225}$Ac, eluting from the substrate $^{213}$Bi produced by bound $^{225}$Ac, coupling the eluted $^{213}$Bi, substantially free of $^{225}$Ac, to a targeting moiety to form a conjugate, said targeting moiety being selected from the group consisting of a ligand having binding specificity for a receptor associated with said target cell or a ligand fragment having binding specificity for a receptor associated with said target cells, and administering said conjugate to said mammal to effectuate specific binding of said conjugate to said target cells.

2. The method as claimed in claim 1, wherein the conjugate is administered intermittently in fractions of the total amount of conjugate required to provide an effective amount of $^{213}$Bi for killing said target cells in the mammal, and wherein a sufficient number of fractions of sufficient quantifies of conjugate are administered to kill essentially all target cells bound by said conjugate, the total quantity of a radiation administered to the mammal being less than the total quantity necessary to kill essentially all target cells by administering a single dose of said conjugate.

3. The method as claim in claim 1, wherein said conjugate is administered continuously for a time sufficient to administer an effective amount of $^{213}$Bi for killing said target cells in the mammal, and wherein a sufficient duration of continuous administration is maintained to kill essentially all target cells bound by said conjugate.

4. The method as claimed in claim 1, wherein said ligand is a peptide.

5. A method for providing site directed radiotherapy to a pathological site in a mammal in need of such therapy, said pathological site comprising a target moiety, said method comprising providing a radioconjugate comprising of a targeting moiety bound, directly or indirectly, to an α-particle emitting radioisotope, wherein the α-particle emitting radioisotope is $^{225}$Ac or $^{213}$Bi, said target moiety and said targeting moiety constituting a specific binding pair, and administering to said mammal a sufficient amount of said conjugate to produce a radiotherapeutic effect at said pathological site, wherein the pathological site comprises a micrometastasis having a diameter of about 1 mm or less.

6. The method of claim 5, wherein said pathological site comprises diseased cells.

7. The method of claim 6, wherein said α-particle emitting radioisotope is $^{213}$Bi.

8. The method of claim 7, wherein said targeting moiety is a ligand having binding specificity for a cell surface receptor present on said diseased cells.

9. The method of claim 8, wherein said ligand is a peptide.

* * * * *